(12) United States Patent
Fini

(10) Patent No.: US 6,287,270 B1
(45) Date of Patent: *Sep. 11, 2001

(54) COMBINED DEVICE COMPRISING A VENOUS BLOOD RESERVOIR AND A CARDIOTOMY RESERVOIR IN AN EXTRACORPOREAL CIRCUIT

(75) Inventor: Massimo Fini, Mirandola (IT)

(73) Assignee: Dideco, S.p.A., Mirandola (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/888,777

(22) Filed: Jul. 7, 1997

(30) Foreign Application Priority Data

Jul. 22, 1996 (IT) .............................. MI96A1529

(51) Int. Cl.$^7$ ..................................................... A61M 37/00
(52) U.S. Cl. .......................................................... 604/6.15
(58) Field of Search ........................ 422/45–48; 604/4–6, 604/4.01, 5.01–5.04, 6.01–6.09, 6.1, 6.11–6.16; 128/DIG. 28

(56) References Cited

U.S. PATENT DOCUMENTS

| | | |
|---|---|---|
| 3,927,980 | 12/1975 | Leonard . |
| 4,006,745 | 2/1977 | Sorenson . |
| 4,490,331 | 12/1984 | Steg, Jr. . |
| 4,642,089 | 2/1987 | Zupkas et al. . |
| 4,664,682 * | 5/1987 | Monzen ................................ 604/406 |
| 4,846,800 | 7/1989 | Ouriel et al. . |
| 4,876,066 | 10/1989 | Bringham et al. . |
| 5,039,430 | 8/1991 | Corey, Jr. . |
| 5,039,482 * | 8/1991 | Panzani et al. ......................... 422/46 |
| 5,049,146 | 9/1991 | Bringham et al. . |
| 5,061,236 | 10/1991 | Sutherland et al. . |
| 5,078,677 | 1/1992 | Gentelia et al. . |
| 5,110,549 | 5/1992 | Gordon . |
| 5,158,533 * | 10/1992 | Strauss et al. .......................... 604/4 |
| 5,186,431 | 2/1993 | Tamari . |
| 5,266,265 | 11/1993 | Raible . |
| 5,270,005 | 12/1993 | Raible . |
| 5,318,510 | 6/1994 | Cathcart . |
| 5,403,273 * | 4/1995 | Lindsay ................................... 604/4 |
| 5,411,705 * | 5/1995 | Thor et al. ............................. 422/45 |
| 5,458,579 * | 10/1995 | Cathcart ................................... 604/4 |
| 5,667,485 * | 9/1997 | Lindsay ................................... 604/4 |

FOREIGN PATENT DOCUMENTS

| | | |
|---|---|---|
| 0 371 173 A1 | 6/1990 | (EP) . |
| 0 587 251 A1 | 3/1994 | (EP) . |

\* cited by examiner

*Primary Examiner*—Sharon Kennedy
*Assistant Examiner*—Catherine Serke
(74) *Attorney, Agent, or Firm*—Popovich & Wiles, P.A.

(57) ABSTRACT

A combined device having a reservoir for venous blood and a reservoir for cardiotomy blood is disclosed. The device is characterized in that the venous reservoir is separated from the cardiotomy reservoir by a partition which includes a plurality of apertures. The apertures are in fluid communication with a plurality of ducts and passageways which are configured to provide various modes of operation depending upon whether, for the particular surgical conditions, it is desired to mix venous and cardiotomy blood, or to isolate those blood pools from each other.

18 Claims, 2 Drawing Sheets

COMBINED DEVICE COMPRISING A VENOUS BLOOD RESERVOIR AND A CARDIOTOMY RESERVOIR IN AN EXTRACORPOREAL CIRCUIT

FIELD OF THE INVENTION

The present invention is in the field of devices for use in surgical procedures. More particularly, the present invention relates to a device having both a venous blood reservoir and a cardiotomy reservoir for use in an extracorporeal circuit.

BACKGROUND OF THE INVENTION

Many surgical operations involve circulating the blood of a patient through an extracorporeal circuit. In particular, many open-heart surgical procedures require that the patient's heart be stopped, and that various biological functions (i.e., blood circulation and oxygenation) be performed mechanically by various devices included in the extracorporeal circuit. In addition to a pump and to the tubing through which the blood will flow, devices including oxygenators, heat exchangers, and blood accumulation reservoirs may be employed. Each of these devices is monitored and managed by persons who may be present in the operating room, or at remote monitoring and control stations.

One type of blood accumulation reservoir used in such procedures is a venous reservoir. The venous reservoir serves as a receptacle for blood, typically blood that has been removed from the patient through a vein, which is subsequently oxygenated and further processed prior to being recirculated back to the patient. Thus, the venous reservoir typically serves to collect blood as it first enters the extracorporeal circuit The use of the venous reservoir enables the operator to control the blood flow rate, blood pressure, blood volume and related parameters necessary to maintaining the patient during the surgical procedure.

A second type of blood accumulation reservoir used in such procedures is a cardiotomy reservoir. The cardiotomy reservoir is used to contain blood which has been collected from the operating field. Blood collected in the cardiotomy reservoir can be reinfused into the patient after being filtered to remove any clots or other unwanted contaminants.

Since the space in the operating room available to operators is often limited, devices have been proposed which combine the venous reservoir and the cardiotomy reservoir in a single structure. In such devices, inlets for the venous blood and for the blood from the operating field are separated from one another. Blood entering the device is filtered and then collected in a common chamber.

These devices, however, are known to have certain disadvantages. For example, the surface area of such devices which comes into contact with the blood is relatively large. As a result, the blood becomes susceptible to damage or coagulation. Additionally, even under relatively normal operating conditions, retrograde blood flow may be induced, causing the blood to be reverse filtered. This is particularly problematic if only venous blood is being collected, because the retrograde flow causes the blood to be sequestered within the cardiotomy filter, thereby reducing the volume of blood available for oxygenation and recirculation to the patient.

OBJECTS AND SUMMARY OF THE INVENTION

One object of the present invention is to provide a combined device having both a venous blood reservoir and a cardiotomy reservoir. Another object of the invention is to provide a device which allows venous blood and cardiotomy blood to be optionally integrated if surgical conditions or requirements warrant. Still another object of the invention is to provide a combined venous blood reservoir and cardiotomy reservoir which minimize blood contact with large surface areas of the device and which eliminate the risk of reverse filtration.

These and other objects of the invention arc achieved by a combined device having a venous blood reservoir and a cardiotomy reservoir. The device is characterized in that it includes a housing having a partition which separates a lower reservoir from an upper reservoir. The lower reservoir is adapted for use as the venous reservoir, and the upper reservoir is adapted for use as the cardiotomy reservoir. The venous reservoir is provided with a blood inlet connector and a blood outlet connector, and the cardiotomy reservoir and is provided with a blood inlet connector and with an air outlet connector. Each of the blood inlet connectors is positioned so that blood entering the device is caused to flow through a defoaming substance and a filter. Additionally, thee partition which separates the venous reservoir from the cardiotomy reservoir is provided with at least two ducts which, starting from apertures formed in the partition, project upward into the cardiotomy reservoir and reach different elevations therein.

BRIEF DESCRIPTION OF THE DRAWINGS

FIG. 4 is a sectional view, taken along the plane IV—IV of FIG. 1.

DETAILED DESCRIPTION OF THE INVENTION

Figure 1:
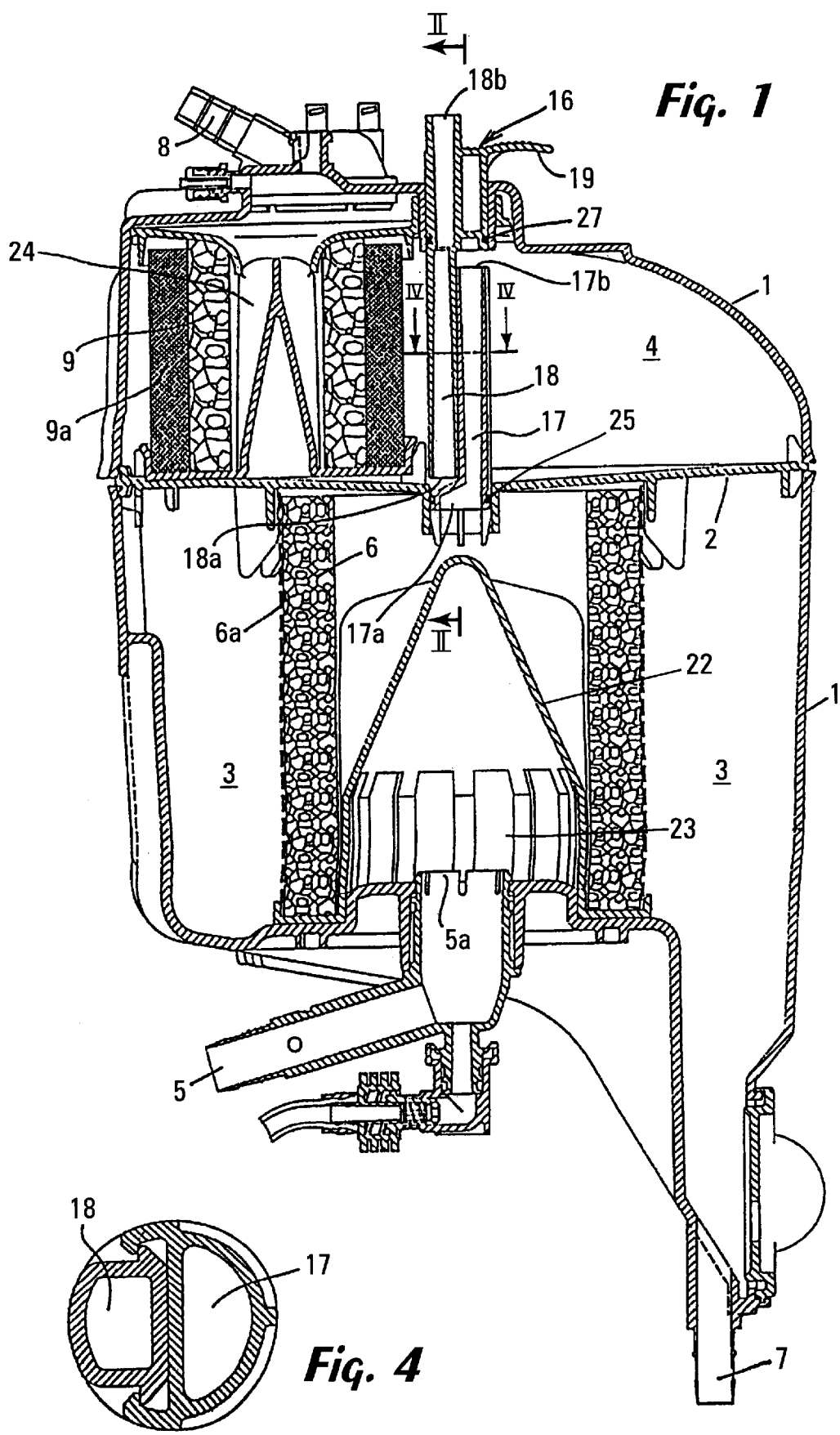
FIG. 1 is a sectional view of one embodiment of the invention, taken along a longitudinal plane.
Figure 2:
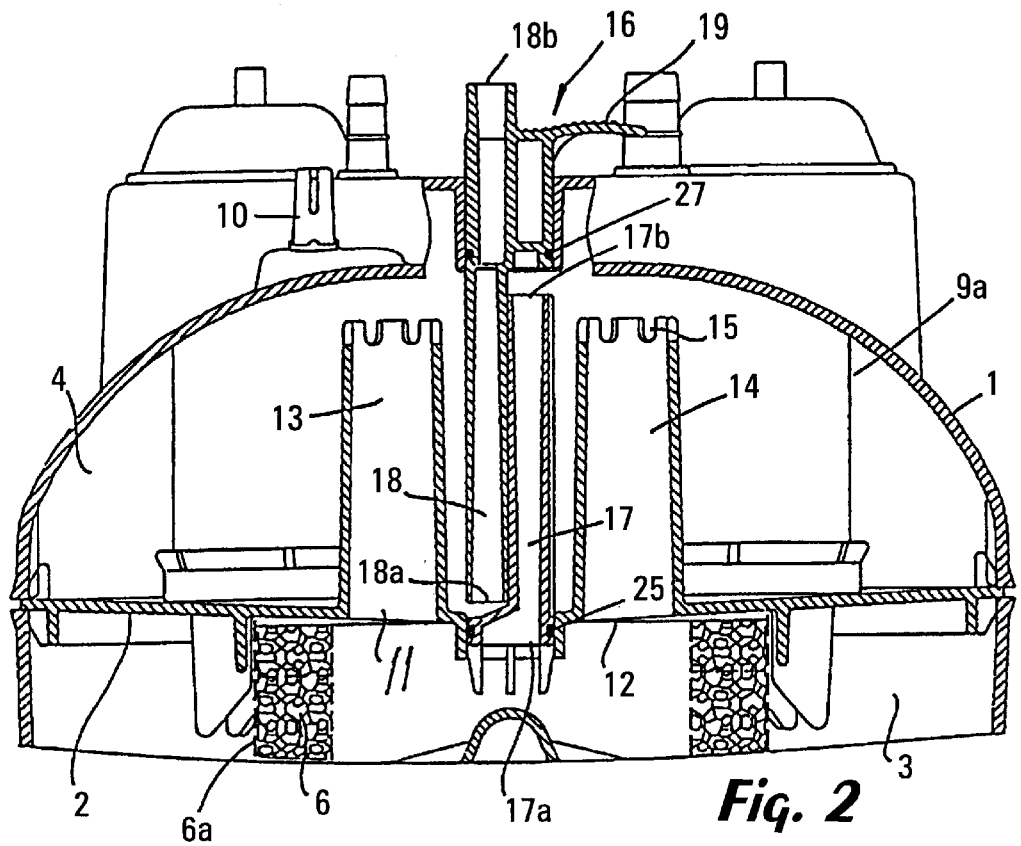
FIG. 2 is an enlarged sectional view, taken along the plane II—II of FIG. 1.
Figure 3:
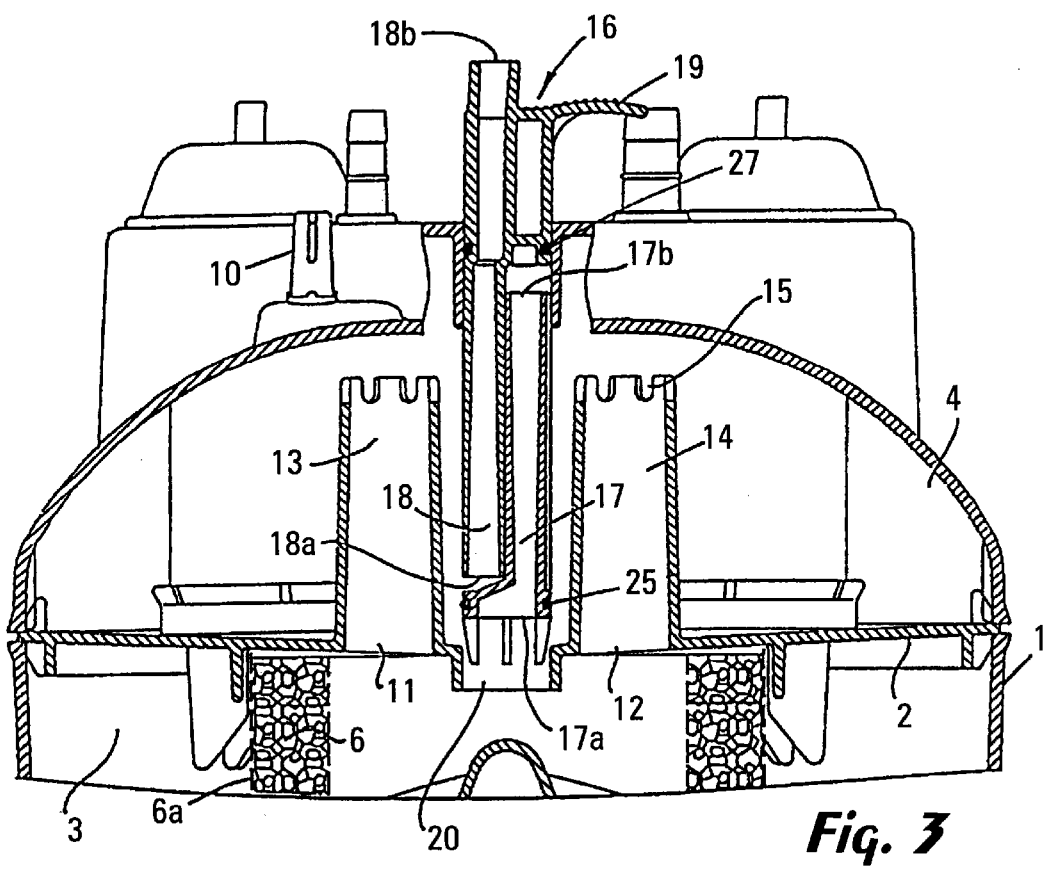
FIG. 3 is the same sectional view of FIG. 2, but with the device in a different operating mode.

One embodiment of the device of the present invention is depicted in FIGS. 1–4. Regarding FIGS. 2 and 3, and for the sake of clarity, a view of the device taken along plane II—II of FIG. 1 is shown. IN FIGS. 2 and 3, the column 16 has been rotated 90° into the page with respect to its position shown in FIG. 1. With reference to the above FIGURES., the reference numeral 1 designates a housing of the device and the reference numeral 2 designates a partition which divides the space enclosed by the housing 1 into a venous reservoir 3, and a cardiotomy reservoir 4. The housing is preferably formed of a transparent polymer to allow the interior of the device to be viewed by an operator. Numerous transparent, medically useful polymers are known to those having ordinary skill in the art.

The venous reservoir 3 is provided with an venous inlet connector 5, terminating at 5a, for the venous blood. Venous blood entering the venous reservoir 3 through the venous inlet connector 5 enters a distribution chamber 22 where it is passed outward, in a substantially uniform manner, into a central region of the venous reservoir through a plurality of slotted apertures 23 formed in the distribution chamber 22. The central region of the venous reservoir is defined by a generally cylindrical wall 6 of a defoaming material. The defoaming material is surrounded by a filter 6a through which the blood must also pass as it enters the venous reservoir 3. Blood exits the venous reservoir 3 through a venous outlet connector 7.

In one embodiment, the defoaming material comprises a porous polymeric material such as a polyurethane foam. In one preferred embodiment, the defoaming material is a polyurethane foam having a pore size of approximately 5 to 50 pores per inch, more preferably approximately 20 to 30 pores per inch. The defoaming material may optionally be treated with a medically acceptable antifoaming agent such as a silicone antifoaming agent. The filter is a screen, preferably formed of a polyester, having an aperture size in the range of about 20 to 50 microns.

The top of the venous reservoir 3 is defined by a partition 2 which separates the venous reservoir 3 from the cardiotomy reservoir 4. The cardiotomy reservoir 4 is provided with a cardiotomy inlet connector 8 for receiving blood arriving from the operating field, and an air outlet connector 10. Blood entering the cardiotomy reservoir 4 through the cardiotomy inlet 8 first encounters a flow distributor 24, which distributes the blood outwardly in a substantially uniform manner. As with the blood entering the venous reservoir, the blood next encounters a generally cylindrical wall 9 of a defoaming material. The defoaming material is surrounded by a filter 9a through which the blood must also pass as it enters the cardiotomy reservoir 4. The defoaming material is as described above, namely, a porous polymeric material such as a polyurethane foam. As before, in one preferred embodiment, the defoaming material is a polyurethane foam having a pore size of approximately 5 to 50 pores per inch, more preferably approximately 20 to 30 pores per inch, and the filter is a screen, preferably formed of a polyester, having an aperture size in the range of about 20 to 50 microns.

The partition 2 which separates the venous and cardiotomy reservoirs is typically a substantially flat plate. When the device is in operation, it is positioned in a manner that maintains the partition in a substantially horizontal orientation. The partition 2 is provided with a plurality of apertures that provide for operation of the device in the manner discussed below.

In one embodiment, shown in FIGS. 1–3, the partition 2 includes two apertures 11 and 12, from which extend two ducts 13 and 14. The ducts preferably extend substantially at right angles to partition 2 and therefore are maintained in a vertical orientation when the device is oriented in its proper operating position. The ducts 13 and 14 extend into the cardiotomy reservoir 4 and reach approximately the same elevation. The upper edge of each duct is typically provided with a plurality of axial notches 15.

An axially moveable column 16 is positioned preferably in the center of the cardiotomy reservoir 4 and extends upward through the housing 1. The column 16 includes a first passageway 17 and a second passageway 18. In the first passageway 17, a lower end 17a communicates with the venous reservoir 3 through a central aperture 20 in the partition 2, and an upper end 17b communicates with the cardiotomy reservoir 4. Likewise, in the second passageway 18, a lower end 18a communicates with the cardiotomy reservoir 4 and an upper end 18b communicates with the exterior of the housing.

Column 16 can be caused to move axially by manual action on tab 19. As such, the column can be moved between a lower stroke limit position, illustrated in FIGS. 1 and 2, and an upper stroke limit position, shown in FIG. 3. While in the lower stroke position, the lower end 17a of the first passageway is sealingly inserted into a central aperture 20 provided preferably at the center of the partition 2. The seal may optionally be enhanced through the use of an O-ring 25 positioned around the exterior of the lower end 17a of the first passageway. The seal, when engaged, serves to prevent blood in the cardiotomy reservoir from entering the venous reservoir. When the seal is engaged, the upper end 17b of the first passageway is caused to be positioned at an elevation which is above that of the upper edges of the ducts 13 and 14. Alternatively, when the column 16 is moved into its upper stroke position, the lower end 17a of the first passageway 17 is extracted from the central aperture 20, thereby disengaging the seal and allowing blood in the cardiotomy reservoir 4 to flow directly into the venous reservoir 3. It should be noted that regardless of the position of the column 16, fluid communication through the second passageway 18 is substantially unaffected. A second O-ring 27 may optionally be provided around the exterior of an upper portion of the column 16. The second O-ring 27 serves to provide a seal between the upper portion of the column and the portion of the housing 1 through which the column passes.

When the column 16 is at the lower stroke limit, i.e., in the position shown in FIGS. 1 and 2, blood flowing into venous inlet connector 5 enters the venous reservoir 3. If the amount of blood entering the venous reservoir is greater than the amount exiting through the venous outlet connector 7, the level of blood inside the venous reservoir 3 is caused to rise. It is possible that the rising level of blood can lead to the complete filling of the venous reservoir. At this point, one advantage of the present invention becomes apparent, since an additional accumulation of blood is allowed because the blood can enter the ducts 13 and 14, as well as tile first passageway 17. Such excess blood can then rise in the ducts and passageway until it overflows into the cardiotomy reservoir 4 through the ducts 13 and 14. By integrating the venous reservoir 3 and the cardiotomy reservoir 4, the device, whenever necessary, allows the accumulation of an amount of venous blood which is far greater than the capacity of the venous reservoir alone.

Integration of the venous and cardiotomy reservoirs also allows air and other gaseous emboli entrained in the venous blood, resulting for example from poor cannulation, to be released from the device by passing through the ducts 13, 14 and the first passageway 17 and allowing it to collect in the upper portion of the cardiotomy reservoir 4, from which it may exit or be withdrawn through the air outlet connector 10.

Likewise, the functionality of the cardiotomy reservoir 4 is also enhanced. Specifically, blood entering the cardiotomy reservoir 4 through the cardiotomy inlet connector 8 gradually rises in that reservoir until it is almost filled. Rather than completely filling the cardiotomy reservoir, however, once the blood reaches a certain level, it is caused to enter the ducts 13 and 14 and flow downward therethrough, accumulating in the venous reservoir 3. As such, the device is configured to allow excess accumulation of either venous or cardiotomy blood.

Even if excess cardiotomy blood is flowing into the venous reservoir, air and other gaseous emboli present in the venous blood can still be removed from the device. Since the upper end 17b of the passageway 17 is configured to remain above the upper edges of the ducts 13 and 14, even if the ducts are communicating blood into the venous reservoir, the passageway 17 remains blood-free and capable of communicating air from the venous reservoir into the cardiotomy reservoir, and ultimately, to the exterior of the housing through the air outlet connector 10.

When the column 16 is positioned at its upper stroke limit, as shown in FIG. 3, all of the blood contained in the cardiotomy reservoir 4 will flow into the underlying venous reservoir 3 through the central aperture 20. As such, in this configuration, the central aperture 20 acts as a drainage port which may be plugged and unplugged by the column 16.

Finally, it should be noted that a situation can arise in which the operator does not wish to mix blood contained in the cardiotomy reservoir 4 with blood contained in the venous reservoir 3. This can occur, for example, if undesirable substances are present in the cardiotomy blood. In that situation, the blood contained in the cardiotomy reservoir is effectively isolated from the blood in the venous reservoir and can be completely removed from the device through passageway 18.

It should be noted that the advantages of the device of the present invention are not intended to be strictly limited to those described above. For example, in the embodiments of the device shown in FIGS. 1–4, the amount of blood contact with the internal surfaces of the device has been minimized, as has the possibility of reverse filtration of blood contained within the device. Furthermore, due to the relatively non-complex design and operation of the device, the device will respond rapidly to control manipulations by the operator.

Of course, the described invention is amenable to numerous modifications and variations, all of which are intended to be within the scope of the inventive concept.

Thus, for example, the number of ducts provided on the partition can be different from the configuration described.

Likewise, the invention is not intended to be limited to the particular materials employed, nor to the shapes or any dimensions employed. Rather, the device may be made according to the specific requirements of a particular application for which its use is intended.

EQUIVALENTS

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A combined blood reservoir which comprises:
   a) a first reservoir for receiving and containing venous blood;
   b) a second reservoir for receiving and containing cardiotomy blood;
   c) the first and second reservoirs being in fluid communication such that either reservoir can overflow into the other, the first reservoir being separated from the second reservoir by a partition, and
   d) a passageway which allows a gas to communicate between the reservoirs, wherein such communication can occur even when one reservoir is overflowing into the other;
   wherein the passageway is moveable between a lower position and an upper position, the passageway being such that when it is moved into the lower position, its lower end sealingly mates with an aperture in the partition to provide fluid communication between the first and second reservoirs through the passageway, and when it is moved into the upper position, it allows fluid communication between the first and second reservoirs through the aperture.

2. A combined blood reservoir which comprises:
   a) a venous reservoir for containing venous blood, the venous reservoir having a venous blood inlet and a venous blood outlet;
   b) a cardiotomy reservoir for containing cardiotomy blood, the cardiotomy reservoir positioned above the venous reservoir and having a cardiotomy blood inlet and a gas outlet;
   c) a partition which separates the venous reservoir from the cardiotomy reservoir, the partition including a plurality of apertures capable of providing fluid communication between the venous reservoir and the cardiotomy reservoir;
   d) at least one duct extending upward from at least one aperture, the duct having an upper outlet contained within the cardiotomy reservoir; and,
   e) at least one passageway having a lower end and an upper end, the lower end of the passageway mating with one aperture in the partition to provide fluid communication between the passageway and the venous reservoir, and further having an upper end which extends into the cardiotomy reservoir to an elevation that is above that of the upper outlet of the at least one duct.

3. The combined blood reservoir of claim 2, wherein the passageway is moveable between a lower position and an upper position, the passageway being such that when it is moved into the lower position, its lower end sealingly mates with one aperture in the partition to provide fluid communication between the passageway and the venous reservoir, and when it is moved into the upper position, it allows fluid communication between the cardiotomy reservoir and the venous reservoir through the aperture.

4. The combined blood reservoir of claim 2, wherein blood entering the venous reservoir through the venous blood inlet is caused to pass through a defoaming substance and a filter.

5. The combined blood reservoir of claim 2, wherein blood entering the cardiotomy reservoir through the cardiotomy blood inlet is caused to pass through a defoaming substance and a filter.

6. The combined blood reservoir of claim 2, wherein blood entering the venous reservoir from the cardiotomy reservoir is caused to pass through a defoaming substance and a filter.

7. The combined blood reservoir of claim 3, wherein the movable passageway is contained within a column that can be manually actuated by an operator.

8. The combined blood reservoir of claim 7, wherein the column includes a second passageway which provides fluid communication between the cardiotomy reservoir and the exterior of the device.

9. The combined blood reservoir of claim 2, wherein the partition comprises a substantially flat plate.

10. The combined blood reservoir of claim 9, wherein the partition is maintained in a substantially horizontal orientation during operation of the device.

11. A combined blood reservoir which comprises:
    a) a venous reservoir for containing venous blood, the venous reservoir having a venous blood inlet and a venous blood outlet;
    b) a cardiotomy reservoir for containing cardiotomy blood, the cardiotomy reservoir positioned above the venous reservoir and having a cardiotomy blood inlet and a gas outlet;
    c) a partition which separates the venous reservoir from the cardiotomy reservoir, the partition including a plurality of apertures capable of providing fluid communication between the venous reservoir and the cardiotomy reservoir, d) at least one duct extending upward from at least one aperture, the duct having an upper outlet contained within the cardiotomy reservoir; and, e) at least one passageway having a lower end and an upper end and being moveable relative to the partition, the passageway being such that when it is moved into a lower position, its lower end sealingly mates with one aperture in the partition to provide fluid communication between the passageway and the venous reservoir, and when it is moved into an upper position, it allows fluid communication between the cardiotomy reservoir and the venous reservoir through the aperture, the passageway further having an upper end which extends into the cardiotomy reservoir to an elevation that is above that of the upper outlet of the at least one duct.

12. The combined blood reservoir of claim 11, wherein blood entering the venous reservoir through the venous blood inlet is caused to pass through a defoaming substance and a filter.

13. The combined blood reservoir of claim 11, wherein blood entering the cardiotomy reservoir through the cardiotomy blood inlet is caused to pass through a defoaming substance and a filter.

14. The combined blood reservoir of claim 11, wherein blood entering the venous reservoir from the cardiotomy reservoir is caused to pass through a defoaming substance and a filter.

15. The combined blood reservoir of claim 11, wherein the movable passageway is contained within a column that can be manually actuated by an operator.

16. The combined blood reservoir of claim 11, wherein the column includes a second passageway which provides fluid communication between the cardiotomy reservoir and the exterior of the device.

17. The combined blood reservoir of claim 11, wherein the partition comprises a substantially flat plate.

18. The combined blood reservoir of claim 17, wherein the partition is maintained in a substantially horizontal orientation during operation of the device.

* * * * *